(12) United States Patent
Landaeta

(10) Patent No.: US 11,501,850 B2
(45) Date of Patent: *Nov. 15, 2022

(54) AUTOMATED FEATURE EXTRACTION USING GENETIC PROGRAMMING

(71) Applicant: Natural Computation LLC, Oakland, NJ (US)

(72) Inventor: David James Landaeta, Oakland, NJ (US)

(73) Assignee: Natural Computation LLC, Oakland, NJ (US)

( * ) Notice: Subject to any disclaimer, the term of this patent is extended or adjusted under 35 U.S.C. 154(b) by 211 days.

This patent is subject to a terminal disclaimer.

(21) Appl. No.: 17/137,934

(22) Filed: Dec. 30, 2020

(65) Prior Publication Data

US 2021/0174896 A1 Jun. 10, 2021

Related U.S. Application Data

(63) Continuation-in-part of application No. 16/763,268, filed as application No. PCT/US2020/015873 on Jan. 30, 2020, now Pat. No. 10,956,129.

(Continued)

(51) Int. Cl.
*G16B 20/40* (2019.01)
*G16B 40/00* (2019.01)
*G16B 50/30* (2019.01)

(52) U.S. Cl.
CPC ............ *G16B 20/40* (2019.02); *G16B 40/00* (2019.02); *G16B 50/30* (2019.02)

(58) Field of Classification Search
CPC ........ G16B 20/40; G16B 50/30; G16B 40/00; G06N 3/126; G06F 8/30; G06F 8/20
See application file for complete search history.

(56) References Cited

U.S. PATENT DOCUMENTS

2003/0177105 A1   9/2003   Xiao
2021/0089336 A1*  3/2021   Jaini .................. G06F 8/36

FOREIGN PATENT DOCUMENTS

EP    1830254 A2 *  9/2007   ............... G06F 8/20
WO    200106358 A1   1/2001
WO    2018224165 A1  12/2018

OTHER PUBLICATIONS

Ronald Garcia et al.; A Comparative Study of Language Support for Generic Programming; ACM; pp. 115-134; retrieved on Aug. 18, 2022 (Year: 2003).*

(Continued)

*Primary Examiner* — S. Sough
*Assistant Examiner* — Cuong V Luu
(74) *Attorney, Agent, or Firm* — Morgan, Lewis & Bockius LLP

(57) ABSTRACT

A method evolves generic computational building blocks. The method initializes a parent population with randomly generated programs or programs evolved by a genetic programming instance that uses randomized targets. The method also obtains a list of randomly generated test inputs. The method generates a target dataset that includes input-output pairs of randomly generated binary strings. The method also applies a fitness function to assign a fitness score to each program, based on the target dataset. The method grows a seed list by applying genetic operators, and selecting offspring that satisfy a novelty condition. The novelty condition is representative of an ability of a program to produce unique output for the list of randomly generated test inputs. The method iterates until a terminating condition has been satisfied. The terminating condition is representative of an ability of programs in the seed list to solve one or more genetic programming instances.

22 Claims, 4 Drawing Sheets

Related U.S. Application Data

(60) Provisional application No. 62/944,468, filed on Dec. 6, 2019.

(56) References Cited

OTHER PUBLICATIONS

Jose Pedro Magalhaes; The Right Kind of Generic Programming; ACM; pp. 13-24; retrieved on Aug. 18, 2022 (Year: 2012).*

Moraglio et al. "Semantic Genetic Programming"; LinkedIn SlideShare; Publication [online]. Jul. 15, 2015 [retrieved Mar. 18, 2020]. Retrieved from the Internet: <URL:https://www.slideshare.net/AlbertoMoraglio/semantic-genetic-programming-tutorial? from_action=save >; pp. 1-100.

International Search Report and Written Opinion dated Apr. 9, 2020 for International Patent Application No. PCT/US2020/015873, 13 pages.

David J. Montana; Strongly Typed Genetic Programming; MIT; pp. 199-230; retrieved on Nov. 2, 2020 (Year: 1995).

William H. Hsu et al.; Evolutionary Tree Genetic Programming; ACM; pp. 1789-1790; retrieved on Nov. 2, 2020 (Year 2005).

* cited by examiner

AUTOMATED FEATURE EXTRACTION USING GENETIC PROGRAMMING

PRIORITY CLAIM AND RELATED APPLICATION

This application is a continuation-in-part of U.S. application Ser. No. 16/763,268, filed May 12, 2020, entitled "Using Genetic Programming to Create Generic Building Blocks," which claims priority to U.S. Provisional Application Ser. No. 62/944,468, filed on Dec. 6, 2019, entitled "Process for Creating Generic Computational Building Blocks," each of which is incorporated by reference herein in its entirety.

TECHNICAL FIELD

The present disclosure relates to genetic programming systems, and in particular, to systems, methods, and devices for automated feature extraction using genetic programming.

BACKGROUND

In machine learning, feature extraction is the process of discovering a transformation of measured data that removes redundancy while preserving information content. The transformed data elements are the so-called features of the original data. By reducing the number of elements required to describe an input dataset, also known as the input dimension, feature extraction decreases the complexity and increases the effectiveness of subsequent steps in machine learning, such as model construction for the purpose of predicting unseen data. Conventional methods for automated feature extraction using genetic programming (GP) cannot be used for unsupervised learning, cannot produce features of arbitrary complexity, and/or the features cannot be expressed in a programming language.

SUMMARY

Accordingly, there is a need for a new approach for automated feature extraction using genetic programming. The techniques described herein have the advantage of making features explainable, since they are described by human-readable computer programs, and, unlike previous such methods using GP, the techniques are appropriate for both unsupervised and supervised learning. Given a training dataset for a machine learning model, the method according to the techniques described herein extracts features of the training dataset by creating generic building blocks. Whenever the method requires a randomly generated input, rather than generating a random string of bits, the method randomly selects an input from the training dataset. The method also extracts features of the training dataset by regarding the seed list as a set of candidate features and applying a feature selection technique to select a subset providing the extracted features. An optional further modification initializes the parent population using generic building blocks previously created, rather than initializing the population randomly.

Various implementations of systems, methods and devices within the scope of the appended claims each have several aspects, no single one of which is solely responsible for the desirable attributes described herein. Without limiting the scope of the appended claims, some prominent features are described. After considering this discussion, and particularly after reading the section entitled "Detailed Description" one will understand how the features of various implementations are used for automated feature extraction using genetic programming.

BRIEF DESCRIPTION OF THE DRAWINGS

So that the present disclosure can be understood in greater detail, a more particular description may be had by reference to the features of various implementations, some of which are illustrated in the appended drawings. The appended drawings, however, merely illustrate the more pertinent features of the present disclosure and are therefore not to be considered limiting, for the description may admit to other effective features.

Figure 1:
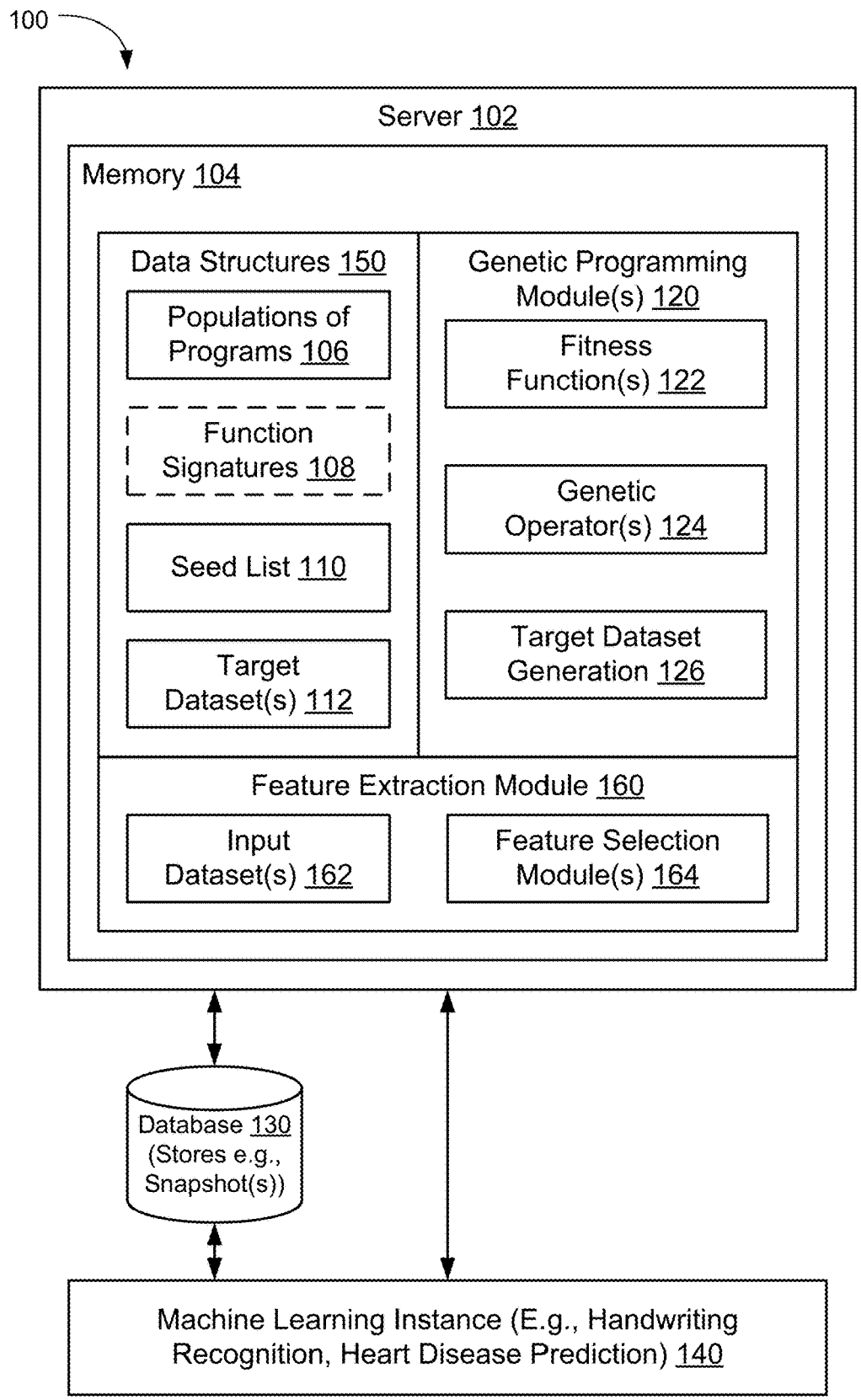
FIG. 1 is a block diagram of a system for using genetic programming to creating generic building blocks for seeding genetic programming instances, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals are used to denote like features throughout the specification and figures.

DETAILED DESCRIPTION

The various implementations described herein include systems, methods, and/or devices that use genetic programming to create generic computational building blocks for seeding genetic programming instances.

Numerous details are described herein in order to provide a thorough understanding of the example implementations illustrated in the accompanying drawings. However, the invention may be practiced without many of the specific details. And, well-known methods, components, and circuits have not been described in exhaustive detail so as not to unnecessarily obscure more pertinent aspects of the implementations described herein.

FIG. 1 is a diagram of a system 100 for creating generic computational building blocks using genetic programming. While certain specific features are illustrated, those skilled in the art will appreciate from the present disclosure that various other features have not been illustrated for the sake of brevity, and so as not to obscure more pertinent aspects of the example implementations disclosed herein.

A GP system may be implemented in a variety of ways, but typically specifies a choice of programming language, a set of genetic operators for recombining parent programs into child programs, a target problem to solve, and a fitness function that determines how well a given program solves the target problem. Typically, a population of programs is initialized with randomly generated code, then the following steps are repeated until some termination criterion is satisfied, such as obtaining a program that exceeds some threshold of fitness:
1. Apply the fitness function to produce a score for each program in the population.
2. Select programs according to their score using a probabilistic method, such as roulette wheel selection.
3. Apply the genetic operators to the selected programs to produce a new population.

Referring back to FIG. 1, the server 102 typically includes one or more processor(s), a memory 104, a power supply, an input/output (I/O) subsystem, and a communication bus for interconnecting these components. Processor(s) execute modules, programs and/or instructions stored in memory 104 and thereby perform processing operations, including the methods described herein according to some embodiments. In some embodiments, the server 102 also includes a display for displaying visualizations (e.g., snapshots or programs).

In some embodiments, the memory 104 stores one or more programs (e.g., sets of instructions), and/or data structures. In some implementations, the memory 104, or the non-transitory computer readable storage medium of the memory 104, stores the following programs, modules, and data structures, or a subset or superset thereof:
an operating system;
generic building block generation module(s) 120 that include:
  fitness function(2) 122, examples of which are described below, in accordance with some embodiments;
  generic operator(s) 124 that include typical operators (e.g., selection, mutation, crossover) used to evolve generations of populations of programs 106 (described below); and
  target dataset generation 126 that generate target datasets 112 (described below);
a feature extraction module 160 that includes:
  input dataset(s) 162. In some embodiments, the feature extraction module 160 normalizes the input dataset (e.g., as described below in the sections describing example use cases); and
  feature selection module(s) 164 that select features from candidate features computed by the genetic programming module(s) 120. The module(s) 164 store the features selected for the input dataset(s) 162, according to some embodiments; and
data structures 150 that include:
  populations of programs 106 that include programs or program fragments (e.g., code snippets) that are self-contained programs (e.g., programs that obey rules of a chosen programming language);
  optionally, function signatures 108 (described below);
  a seed list 110 which is a an output of the generic building blocks generation module 120) that is used to seed genetic programming instances, as described below; and
  target dataset(s) 112 described below.

The above identified modules (e.g., data structures, and/or programs including sets of instructions) need not be implemented as separate software programs, procedures, or modules, and thus various subsets of these modules may be combined or otherwise re-arranged in various implementations. In some embodiments, memory 104 stores a subset of the modules identified above.

In some embodiments, a database 130 (e.g., a local database and/or a remote database) stores one or more modules identified above and data associated with the modules. Furthermore, the memory 104 may store additional modules not described above. The database 130 stores snapshots of the programs 106, the function signatures 108, the seed list 110, and/or the target datasets 112. In some embodiments, the modules stored in memory 104, or a non-transitory computer readable storage medium of memory 104, provide instructions for implementing respective operations in the methods described below. In some embodiments, some or all of these modules may be implemented with specialized hardware circuits that subsume part or all of the module functionality. One or more of the above identified elements may be executed by one or more processor(s).

Some embodiments include an I/O subsystem that communicatively couples server 102 to one or more devices such as client devices, the database 130, via a local and/or wide area communications network (e.g., the Internet) via a wired and/or wireless connection. Some embodiments include a communication bus that optionally includes circuitry (sometimes called a chipset) that interconnects and controls communications between system components.

The programs in the seed list 110, and/or the snapshots stored in the database 130 are used to seed and/or test genetic programming instances 140. Examples of genetic programming instances 140 include image processing or recognition of handwritten text (described below). In some embodiments, the instances 140 store genetic programming instances that are used to determine if the seed list 110 satisfies a terminating condition (examples of which are described below).

Example Method for Using Genetic Programming to Create Generic Building Blocks

A method uses genetic programming to create generic building blocks for seeding genetic programming instances, in accordance with some embodiments. The method or the process (sometimes referred to as code farming) is an instance of GP. The method produces program(s) whose input-output pairs match as closely as possible a given dataset of input-output pairs that is randomly generated. Some embodiments randomly generate a new target dataset with each new generation of the population of programs. In some embodiments, the population evolves, with a variety of possible solutions present at all times.

There is wide latitude on the properties of a GP instance that can successfully implement this process. Some embodiments require that (i) the programming language is Turing complete, meaning that it can encode any function that a Turing machine can encode, (ii) the genetic operators implement some form of sexual recombination; for example crossover, and (iii) the weak selection assumption applies, meaning that the variation in fitness between genotypes is small compared to the recombination rate. The requirement (i) ensures the reusability of the building blocks discovered by the process. The requirements (ii) and (iii) ensure programs are generic building blocks.

In some embodiments, the process produces generic building blocks that are program fragments. In some embodiments, instead of identifying specific fragments within a population of programs as building blocks, entire programs produced by the process are used as building blocks. In some embodiments, as long as the correct building blocks are present somewhere in the population, the GP mechanics determines or selects and combines the building blocks into a solution for a GP instance.

In some embodiments, whenever a new instance of GP is to be seeded with generic building blocks, its initial population is chosen from the programs that were produced by the code farming process. Some embodiments select programs from the last generation of programs produced by the process. Some embodiments select building blocks from the collection of programs by taking the most fit program in each generation of the process, with preference given to later generations. Some embodiments apply a fitness function with each generation of the process, and make a copy of the program with the highest fitness score. In some embodiments, ties are broken arbitrarily. Some embodiments add the most fit program to the end of a persistent list of programs, called a seed list, which is initially empty. In some embodiments, if a new GP instance requires an initial population of size n, then the last n entries on the seed list are selected. In some embodiments, the seed list is the end product of the process.

Some embodiments apply a filter to the seed list to remove duplicate phenotypes (i.e., function encoded by the program) before using the list to initialize a population. The filtering step helps in restricting the size of the population. Some embodiments use a technique of using function signatures, as described below, to detect duplicate phenotypes in a probabilistic sense.

A well-known problem with GP is that a randomly generated program in any sufficiently rich programming language—especially one that is Turing complete—will tend to encode a function that is trivial, such as a function that always ignores its input and produces constant output. This means that the GP system might never get aloft; in other words, it might never produce interesting behavior. Furthermore, even if non-trivial behavior is produced, it tends to be fragile, in that it is easily destroyed by genetic operators, so the system might not stay aloft. In theory, the probability of getting and staying aloft can be increased by maintaining a sufficiently large population of programs, but this might require vast computational resources. Some embodiments use some of the techniques described below for staying aloft.

In some embodiments, certain highly fit individuals or programs are given added assurance of surviving from one generation to the next. In various embodiments, the ideas described herein can be implemented using a seed list.

In some embodiments, a small subset of the current population is given a higher than normal probability of surviving from one generation to the next. In some embodiments, a seed list, separate from the current population grows by adding copies of programs from the current population that satisfy a novelty condition.

In some embodiments, a seed list participates in a parent selection process in an unusual way. In conventional genetic programming, a roulette wheel is spun to select the next parent from the current population. In accordance with some embodiments, before spinning the wheel, a biased coin is flipped (e.g., to create a Bernoulli distribution) with a small probability (e.g., probability=$1/16$) of obtaining heads. If the coin does come up heads, then some embodiments do not spin the wheel for this parent selection, and do not select the parent from the current population. Instead, some embodiments select the parent from the seed list using a uniform probability distribution (i.e., each program on the seed list equally likely to be selected). On the other hand, if the coin comes up tails, then some embodiments proceed as normal to spin the wheel to select the parent from the current population. In some embodiments, this whole process is repeated with every selection of a parent.

In some embodiments, the seed list is the end product of the process (sometimes called code farming). In some embodiments, the programs that are most recently added to the seed list is considered more useful for seeding GP instances than programs that were added earlier.

In some embodiments, the seed list is persistent over all generations and is initially empty. With each generation, after the fitness function is applied to the current population, all programs (sometimes called individuals) from the current population that satisfy the following conditions are added to the seed list.

a. It is an individual that is not obviously trivial (as described below).
    b. The function it encodes is distinct from that encoded by any other program in the seed list. This is determined efficiently in a probabilistic sense by randomly generating a persistent list of test inputs during system initialization, and declaring a candidate function to be distinct if and only if it has a distinct sequence of outputs for the test inputs. This sequence of outputs is sometimes referred to as the function's signature.

In some embodiments, in order to provide some assurance that non-trivial functions are added to the seed list at all, the fitness function is modified to flag obvious cases of programs encoding trivial functions, which are then assigned the lowest possible score. Some embodiments use automated syntactic analysis of the program to determine that the input will never be read, so the program can be flagged as trivial without ever running it. Syntactic analysis determines if a program has no read instructions, or any such instructions are obviously unreachable. Obviously trivial programs include programs that terminate abnormally when an attempt is made to run it. This includes any program that exceeds computational resource limits, such as memory space or total run time. Some embodiments assign the lowest possible fitness score to such programs in order to promote error-free programs.

As described above, the advantage given to programs in the seed list is that with a small probability, the selection of an individual to be a parent for the next generation comes from the seed list rather than the current generation, and in that case every program in the seed list has equal probability of being selected.

Measuring Progress

Some embodiments measure progress and determine if enough progress has been made to terminate the process using some of the techniques described in this section.

Some embodiments use size of the seed list. For example, if the seed list is growing at a steady pace, then steady progress is being made. In some embodiments, if there is at least a predetermined number of programs in the seed list (e.g., a few thousand programs), then the process terminates.

In some embodiments, a more reliable, although a more resource-intensive, approach is used to periodically (e.g., every few hundred iterations of the process) use copies of the seed list to initialize populations within a test suite of GP instances representing a variety of problems. Some embodiments determine if the test results are improving over time. If the test results provide acceptable solutions, then the process is terminated.

Snapshots

Some embodiments load or save a snapshot of the system, which consists of data needed to allow the process to pause and resume at a later time. In some embodiments, a snapshot contains some or all of the following elements:

The current population of programs and their fitness scores.

The seed list and the corresponding signatures.
The list of test inputs for determining signatures.

Target Datasets

In some embodiments, a target dataset is randomly generated with each new generation of the process. In some embodiments, the target dataset consists of input-output pairs. Some embodiments determine a format for the input-output pairs by trading off various factors that include (i) degree to which an end product (e.g., the seed list) is reusable in various contexts and (ii) the speed and efficiency with which it can be produced. For example, if the end product needs to be reusable for a wide range of problems, then the input-output pairs are pairs of binary strings that have no length restriction apart from being finite, since such strings can encode any information. Some embodiments use a probability density function, which is a variation of the well-known uniform density function, to randomly generate a binary string of arbitrary length. Some embodiments use a probability density function defined by $L(x)=2^{-2l(x)-1}$, where x is any arbitrary string of length l(x).

Some embodiments restrict input-output pairs to a format that is appropriate for a particular problem domain, while still randomly generating the input-output pairs. For example, some embodiments generate a random dataset that is appropriate for the problem domain of image classification using pure Gaussian noise as input and uniformly random labels as output.

Domain-Specific Target Datasets

This section describes domain-specific aspect of target datasets, and subsequently describes the random aspect of the target datasets, for ease of explanation.

For domain-specific aspect of target datasets, in any problem domain, suppose an input is identified with a sequence of real numbers $X=(x_1, \ldots, x_n)$, and the corresponding output is similarly identified with the sequence of real numbers $Y=(y_1, \ldots, y_m)$. For example, in image classification, each $x_i$ might represent a pixel intensity, with n being the number of pixels in the input image. In this case, m is the number of distinct labels that an image can have, with $y_j$ being the probability that the input image has the jth label.

Next, to understand random aspect of target datasets, irrespective of the problem domain, imagine an enormous dataset D of all the input-output pairs that might be interesting. Suppose a uniformly random selection of an input-output pair (X, Y) is obtained from D. Each $x_i$ in X will have a well-known probability distribution $p_i(x)$, and similarly each $y_j$ in Y would have a well-known probability distribution $p_j(y)$. Then, to randomly generate an input-output pair $(X_{rand}, Y_{rand})$ for this domain, some embodiments randomly generate each $x_i$ in $X_{rand}$ and each $y_j$ in $Y_{rand}$ according to their respective probability distributions. By repeating this process t times, some embodiments randomly generate a dataset $Drand=((X_1, Y_1), \ldots, (X_t, Y_t))$. For image classification, for example, $p_i(x)$ is a Gaussian distribution over the range of all possible pixel intensities, and $p_j(y)$ is a Gaussian distribution over the range of all possible probabilities (i.e., 0 through 1).

Fitness Function

A fitness function represents the probabilistic nature of genetic programming (GP). Instead of a criteria being satisfied or not, GP assigns each program a fitness score that measures the degree to which the program satisfies the criteria. This is sometimes called "applying the fitness function". The score typically falls within a range of real numbers. Programs with higher scores are more likely to be selected as parents for the next generation than programs with lower scores. However, even a program with the lowest possible score has a greater than zero probability of being selected as a parent, so such a program may or may not be discarded.

In some embodiments, the fitness function measures how well the function encoded by a given program matches the current target dataset. In some embodiments, the fitness function satisfies the weak selection assumption, which means that the fitnesses of all genotypes (programs) are close to one another, say within the interval $[1-\varepsilon, 1+\varepsilon]$, and so the fitness of a genotype g can be written as $F_g=1+\varepsilon\Delta_g$, where $\varepsilon$ is the selection strength, assumed to be small, and $\Delta_g \in [-1, 1]$ is called the differential fitness of the genotype. In some embodiments, these requirements are satisfied by defining $\Delta_g$ appropriately. For example, $\Delta_g=-1$ means that g provides the worst match for the target dataset relative to other members (i.e., programs) of the population, and $\Delta_g=1$ means that g provides the best match relative to other members of the population. In other words, the fitness function assigns a differential fitness value between −1 and 1 to a given program in order to measure how well the program agrees with the target dataset, with larger values denoting better agreement.

Some embodiments use a relaxed definition for what is considered a match. Some embodiments consider degree of correlation between outputs rather than requiring an exact match between the outputs. Some embodiments use this strategy so as to increase the chances of finding an acceptable solution. For example, some embodiments consider a program that produces the exact opposite (in a bitwise sense) of the target output to be as fit as an exact match, given that it is easily transformed into a perfect solution.

Suppose the target dataset is the sequence of input-output pairs $D=((X_1, Y_1), \ldots, (X_t, Y_t))$, and suppose the given program encodes a function f. For each pair (X, Y) in D, X is a sequence of real numbers $X=(x_1, \ldots, x_n)$, and Y is a sequence of real numbers $Y=(y_1, \ldots, y_m)$. The function f is a function that can accept X as input, producing as output the sequence $Y'=(y_1', \ldots, y_m')$. Some embodiments measure the agreement between Y and Y', and then aggregate such values over every (X, Y) in D in order to produce the differential fitness value d. Some embodiments make use of the fact that each $y_j$ in Y has a well-known probability distribution $p_j(y)$, and therefore each $y_j$ has a well-known mean value $u_j$. The range of possible values for $y_j$ can be thought of as being partitioned into two pieces, with the right partition containing all values that are greater than the mean, and the left partition contains all values that are less than or equal to the mean. Some embodiments define that a value $y_j$ is "in agreement with" a value $y_j'$ if both values are in the same partition.

Some embodiments use the following algorithm for computing the differential fitness d:
1. Initialize a real variable r to 0.
2. For each (X, Y) in D do the following:
   a. Compute Y' as described above.
   b. For each position j between 1 and m do the following:
      i. If yj is in agreement with yj' then add 1 to r,
      ii. Else subtract 1 from r.
3. Compute d=absolute_value(r)/(m*t).

This algorithm results in a value for d that is between 0 and 1. Some embodiments compute the fitness score as: $F=1+(e*d)$, where e is the selection strength, which is assumed to be a small positive constant value.

In other words, when F is viewed as a discrete random variable it should have the same mean and the same variance for every computable function f. It is also required that a function f should always be assigned the same fitness score as its inverse function, if such a function exists.

Probabilistic Selection

Some embodiments use a probabilistic selection method (sometimes called "roulette wheel selection" or "fitness proportionate selection"). The selection of a parent is made by spinning a roulette wheel with each program in the population allocated an amount of space on the wheel that is proportional to its fitness score. In other words, spin the wheel enough times to select all of the parents for the next generation. This step is often just called "selection", and it is often regarded as one of the genetic operators like mutation or crossover.

Some embodiments use other methods of selection (e.g., tournament selection that is very popular in off-the-shelf GP software).

Generic Building Blocks

In some embodiments, evolution in the presence of sexual recombination maximizes the mixability of alleles (i.e., program fragments) within the population. The mixability of an allele of a particular gene (i.e., locus of the program fragment) is the degree to which that allele can combine with alleles of other genes to form highly fit individuals. If the fitness of an individual program is based on how well it matches a randomly generated dataset relative to other individuals in the population, then an allele with high mixability corresponds exactly to a generic computational building block. If weak selection is present along with sexual recombination, then the mixability of an allele is measured in a cumulative sense over all generations. Thus, an allele with high mixability corresponds to a code fragment that is present in a family of programs providing good solutions to a wide variety of problems. Such alleles are generic building blocks.

Figure 2:
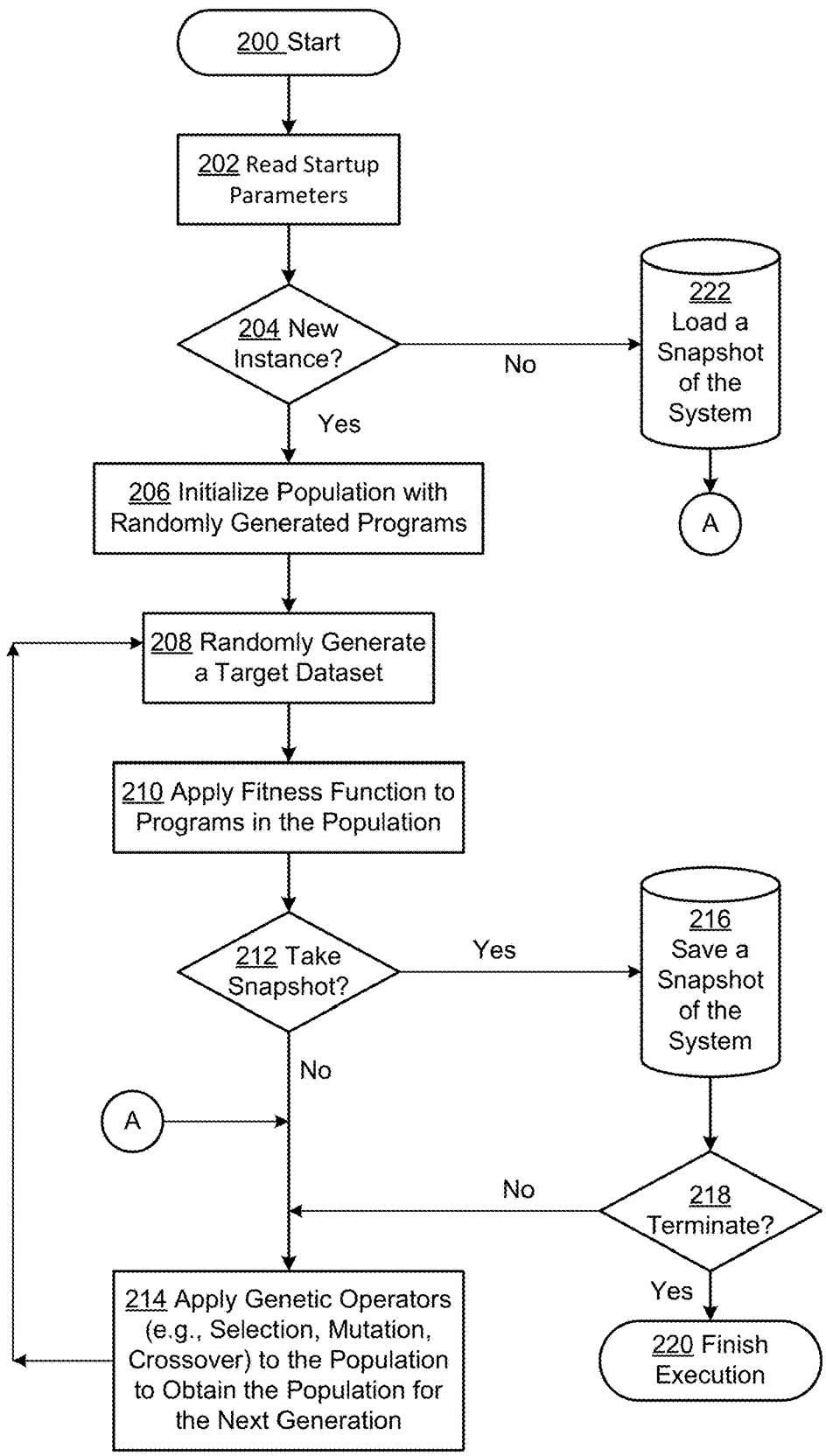
FIG. 2 is a flowchart of a method for using genetic programming to create generic building blocks for seeding genetic programming instances, in accordance with some embodiments.

FIG. 2 is a flowchart of a method for using genetic programming to create generic building blocks for seeding genetic programming instances, in accordance with some embodiments. The method is performed by a server (or processors of the server), such as the server 102, according to some embodiments. The steps in the flowchart shown in FIG. 2 use the techniques described above. In some embodiments, the method starts (200) by reading (202) start-up parameters (e.g., a set of parameters for a concerned domain, maximum size of programs, maximum number of iterations of the process, etc.). Example of start-up parameters are provided below in the section titled "Example Creation and Use of Generic Building Blocks for Image Classification," according to some embodiments. Some embodiments determine (204) whether to generate a new instance of the process (to obtain the seed list). If this is not a new instance, the process loads (222) a snapshot of the system (described above).

Some embodiments initialize (206) a population (e.g., the population of programs 106) with randomly generated programs (described above). Some embodiments also randomly generate a target dataset (described above, e.g., using the target dataset generation module 126). Some embodiments apply (210) a fitness function (described above, e.g., using the fitness function module 122) to programs in the population. Some embodiments determine (212) whether to take or capture a snapshot (described above), and if it is so determined, save (216) or store a snapshot of the system (e.g., to the database 130). Some embodiments determine (218) if a terminating condition is satisfied. For example, the seed list in the snapshot is used to test whether the seed list solves one or more genetic programming instances. If the terminating condition is satisfied, the method finishes (220) execution. If not, the process continues, to apply (214) genetic operators (e.g., selection, mutation, crossover) to the population to obtain the population for the next generation. The process (i.e. steps 214, 208, 210, 212, 216, and 218) is repeated until the terminating condition is satisfied.

According to some embodiments, a method evolves generic computational building blocks. The method is performed by a server (or a computer). For example, the method is performed the server 102 (or one of the modules of the server 102). The method initializes a parent population with randomly generated programs that encode functions. The method also includes obtaining a list of randomly generated test inputs. The method generates a target dataset that includes input-output pairs of randomly generated binary strings. The method also applies a fitness function to assign a fitness score to each program in the parent population. The fitness score represents at least an ability of programs to match the input-output pairs of the target dataset. The method also initializes a seed list with copies of the programs in the parent population that satisfy a novelty condition. The novelty condition is representative of an ability of a program to produce distinct and unique output for the list of randomly generated test inputs. The seed list includes generic program building blocks for seeding an initial population for genetic programming. The method also includes determining if a terminating condition of the seed list has been satisfied. The terminating condition is representative of an ability of one or more programs in the seed list to solve one or more genetic programming instances. In accordance with a determination that the terminating condition has not been satisfied, the method applies at least one genetic operator to the parent population to obtain a current offspring population of programs. The at least one genetic operator includes operators applied to the parent population to grow the seed list, based on fitness scores of programs, to solve the one or more genetic programming instances. The method also includes repeating steps of: (i) generating a new target dataset that includes input-output pairs of randomly generated binary strings; (ii) applying the fitness function to assign a new fitness score to each program in the current offspring population (the new fitness score represents at least an ability of programs to match the input-output pairs of the new target dataset); (iii) appending, to the seed list, copies of the programs in the current offspring population that satisfy said novelty condition; and (iv) applying the at least one genetic operator to the current offspring population to obtain a new offspring population of programs and setting the new offspring population of programs as the current offspring population, until said termination condition is satisfied.

In some embodiments, the method further includes using the seed list to initialize populations within a test suite of genetic programming instances representing a plurality of problems; and determining if the termination condition has been satisfied based on test results of the test suite.

In some embodiments, the method further includes, when applying the at least one genetic operator to the current offspring population, selecting, based on a Bernoulli distribution, programs in the seed list over programs in the current offspring population, as parents. Each program in the seed list is equally liked to be selected as a parent.

In some embodiments, determining if a program satisfies the novelty condition is based on a determination that a program encodes a function that generates a sequence of outputs, for the randomly generated test inputs, that is distinct from sequences of outputs generated by functions encoded by programs in the seed list, for the randomly generated test inputs.

In some embodiments, the method further includes: determining and storing, for each program in the seed list, function signatures that include sequences of outputs generated by functions encoded by the program for the randomly generated test inputs; and retrieving the function signatures. In some such embodiments, determination that the program encodes a function that is distinct from functions encoded by programs in the seed list is further based on a determination that the program encodes a function that generates a sequence of outputs, for the randomly generated test inputs, that is distinct from the function signatures.

In some embodiments, the terminating condition depends at least on size of the seed list (e.g., thousand programs then the method stops).

In some embodiments, the terminating condition depends at least on a determination if the seed list is growing at a predetermined growth rate.

In some embodiments, the method further includes breaking ties arbitrarily when applying the fitness function.

In some embodiments, the method further includes discarding programs from the seed list that encode trivial functions that do not read input, when initializing the seed list and appending to the seed list.

In some embodiments, the method further includes performing syntactic analysis to identify programs that encode trivial functions that do not read input.

In some embodiments, the method further includes discarding programs from the seed list that encode functions that have abnormal runtime behavior (e.g., programs that terminate abnormally when an attempt is made to run) or have abnormal resource requirements (e.g., programs that exceed computational resources limits, such as memory space or total runtime), when initializing the seed list and appending to the seed list.

In some embodiments, the method further includes seeding an initial population for a new instance of genetic programming using a predetermined number of programs in the seed list. In some embodiments, the programs most recently added to the seed list are preferred over earlier ones when seeding an initial population In some embodiments, the at least one genetic operator is one or more of a selection operator, a mutation operator, and a crossover operator.

In some embodiments, each input of the input-output pairs of randomly generated binary strings is generated based on an input probability distribution, and each output of the input-output pairs of randomly generated binary strings is generated based on an output probability distribution. In some embodiments, the input probability distribution is a Gaussian distribution over range of pixel intensities, and the output probability distribution is a Gaussian distribution over [0.0, 1.0].

In some embodiments, the fitness function assigns same fitness score to programs that encode functions that produce bitwise opposite output for same input. In other words, in some embodiments, a program that produces exact opposite (in a bitwise sense) of the target output is as fit as an exact match.

In some embodiments, the fitness function assigns a fitness score between −1 and 1 to a program in order to measure a degree of match between an output of the program and a target dataset, with larger values denoting higher degree of match.

In some embodiments, the one or more genetic programming instances includes a genetic programming instance for partial classification of handwritten digits (described below), and the input-output pairs of randomly generated binary strings are generated based on images from MNIST database, and the method further comprises terminating the method after iterating 2000 times.

Example Creation and Use of Generic Building Blocks for Image Classification

This section describes example creation and use of generic building blocks for image classification, according to some embodiments. Typically, an image is associated with one or more labels. For illustration, suppose an image can have only one of two labels. Image data is simplified so that each pixel value is a single bit. For example, each pixel is either black (0) or white (1). Further suppose each image is exactly 28 rows by 28 columns of pixels. A dataset in this domain has the form $D=((X_1, y_1), \ldots, (X_t, y_t))$. Each (X, y) in D is an input-output pair with X representing an input image $X=(x_1, \ldots, x_n)$, where n=28×28=784, each $x_i$ is a single bit (0 or 1) denoting the intensity of the pixel at position i, and y is a single bit representing the label associated with image X.

In a first phase, some embodiments create generic building blocks via the process described above in reference to FIG. 2, using parameters that are appropriate for this domain. Subsequently, in a second phase, some such embodiments use the end product from the first phase (e.g., the seed list) to seed the initial populations in a test suite of two instances of GP representing specific problems in this domain.

Suppose the programming language used for GP instances in this experiment is the language of Perceptron Turing Machines (PTMs), as described in the Appendix. The language is Turing complete and allows for a form of neuro-evolution, meaning that each program generates an artificial neural network (ANN). The relevant PTM configuration parameters that are common to all GP instances are as follows:

The number of states is 512.

The number of tapes is 2, with each tape having a length of 5 bits, so as to encode either a row index or a column index of an image. Both tapes are input index tapes, and there are no output index tapes since the output is a single bit.

Every program has a fixed length of 4,096 instructions.

Set resource limits on the ANN generated by a program as follows.

The maximum number of nodes is 50,000.

The maximum depth is 100.

The maximum fanout is 16.

If a resource limit is exceeded, it is considered to be an error, in which case the program is assigned the lowest possible fitness score.

The following genetic operators are also common to all GP instances used in this experiment.

Use uniform crossover at a rate of 0.5 operating on a gene-by-gene basis.

Use a permutation operator at a rate of 0.003 operating genotype-wise. That is, for each offspring, with a probability of 0.003, its genes are randomly permuted.

Use a mutation operator at a rate of 0.001 operating gene-wise. That is, for each gene of each offspring, with a probability of 0.001, the allele is changed to a different allele.

Example Phase 1: Creating Generic Building Blocks

The GP instance for the process is set up as follows.
The population size is 1,024.
Use 32 for the number of input-output pairs in the randomized target.
The natural probability distribution to use for both the input pixel values and the output label values in the randomized target is a Bernoulli distribution with the values 0 and 1 equally likely (each having probability 0.5).
Use 32 for the number of test inputs used to generate function signatures.
Use 0.5 for the selection strength.
Use 0.0625 for the probability of selecting a parent from the seed list rather than the current population.
Terminate the process when 200,000 seeds (i.e., programs in the seed list) are found.

The process is iterative, and, in some instances produces several hundred programs for each generation. For example, iterating the process 2,289 times (i.e., 2,289 generations) produces 200,000 seeds.

Example Phase 2: Partial Classification of Handwritten Digits

For the test suite, some embodiments use two GP instances that are designed to solve variants of a simplified form of classifying handwritten digits. Rather than attempting to recognize all digits 0 through 9, the simplified problem (sometimes called partial classification) only attempts to recognize two of the ten digits. Suppose GP instance A attempts to distinguish between digits 0 and 1, and GP instance B attempts to distinguish between digits 6 and 7.

For the training and test datasets, some embodiments use subsets of the MNIST database, which contains scanned images of handwritten digits, together with their correct classifications. The images is divided into training and test datasets (e.g., with 60,000 and 10,000 images, respectively). The images are grayscale and 28 by 28 pixels in size. Some embodiments reformat all images so that each pixel value, which originally ranges from 0 to 255, is translated to a single bit, with 0 corresponding to the interval [0, 127] and 1 corresponding to [128, 255]. GP instance A uses the subset of training and test datasets containing only images of digits 0 and 1, and, GP instance B only uses images of 6 and 7.

Both GP instances A and B have the following configuration properties:
In some embodiments, the training and test datasets are randomly partitioned into mini-batches of size t=32 each. With every generation, the next training mini-batch D is chosen in rotating order, and it is used as the basis for the fitness score for that generation.
To assign a fitness score F to a program g in the current population, some embodiments first compute a differential fitness d as follows.
Initialize a real variable r to 0.
For each (X, y) in D do the following:
  Run program g on input image X.
  If g runs to completion and produces output y, then add 1 to r.
  Else subtract 1 from r.
Compute d=r divided by t.
This gives d a value between −1 and 1. The fitness score is $F=1+\varepsilon d$, where $\varepsilon$ is the selection strength, which has a constant value of 0.5.
The population size is 256.
The termination condition is as follows. With every generation, the program g with the largest fitness score (where ties are broken arbitrarily) is scored again, but each time using the next mini-batch from the test dataset in rotating order. If g receives a perfect score on both training and test mini-batches, then the process terminates successfully with g being the solution. If no such solution is found within 2000 generations, then the process terminates as a failure.

In addition, each GP instance has the option of initializing its population either randomly (a random mode of initialization) or using the last 256 programs (or seeds) produced in Phase 1 (a seed mode of initialization). Some embodiments run each GP instance A and B a predetermined number of times (e.g., 10 times), in each mode. In one experiment, the results obtained are as shown below:
  GP instance A in random mode produced 1 success and 9 failures.
  GP instance A in seed mode produced 8 successes and 2 failures.
  GP instance B in random mode produced 0 successes and 10 failures.
  GP instance B in seed mode produced 6 successes and 4 failures.

In this way, the process described above in reference to FIG. 2 provides a significant performance improvement (over traditional ways of seeding populations) for these GP instances.

Example Application for Learning Numerical Relations

This section describes example creation and use of generic building blocks for learning numerical relations, according to some embodiments. Suppose the problem is to find a computer program that can determine if a given sequence of real numbers satisfies the condition for membership in a particular relation. In some embodiments, for training purposes, there exists a dataset of examples of sequences that do satisfy the relation as well as examples of sequences that do not satisfy the relation. A dataset in this domain has the form $D=((X_1, y_1), \ldots, (X_t, y_t))$. Each (X, y) in D is an input-output pair with X representing an input sequence $X=(x_1, \ldots, x_n)$, where n is a fixed positive integer determined by the relation, each $x_i$ is a real number with an associated probability distribution pi (x) that is determined by the relation, and y is a single bit indicating whether X is in the relation (y=1) or X is not in the relation (y=0).

For example, a stock trader might develop such a dataset, where X is the information in a company's balance sheet, and y is an indication of whether the company's stock should be bought or sold. In this experiment, for the sake of explanation, suppose n=3, and suppose further that a Gaussian distribution (with mean 0 and variance 0.5) is used for each of $x_1$, $x_2$, $x_3$. The output y has a Bernoulli distribution with the values 0 and 1 equally likely (each having probability 0.5).

In some embodiments, there are two phases. In a first phase, some embodiments create generic building blocks via the process described above in reference to FIG. 2, using parameters that are appropriate for this domain. Subsequently, in a second phase, some embodiments use the end product from Phase 1 (the seed list) to seed the initial populations in a test suite of two instances of GP representing specific problems in this domain. As described later, a comparison of the results to those obtained by a traditional approach of seeding the initial populations randomly shows the benefits of the process described above in reference to FIG. 2.

Suppose the programming language used for all GP instances in this experiment is the Slash/A language developed by Artur B. Adib, described in "Slash/A: A programming language and C++ library for (quantitative) linear genetic programming," 2011, disclosure of which is incorporated in its entirety herein by reference. The Slash/A language is a Turing complete imperative programming language that is ideal for implementing numerical relations, because all inputs and outputs are real numbers in double precision floating-point form. The following example reads two inputs, adds them together, and returns the result as an output.

```
input/     # get the next number from the input buffer and save it to
           register F
0/         # set register I = 0
save/      # save content of F into data vector D[I] (i.e. D[0] := F)
input/     # get another input, save to F
add/       # add to F current data pointed to by I (i.e. F := F + D[0])
output/.   # append F to the output buffer
```

Slash/A is implemented as a C++ library, which includes a function for transforming a program given in text form (e.g., text above) into bytecode form, which is an array of unsigned integers, with each unsigned integer mapping to a unique instruction in the language. It is the bytecode form that is used by the Slash/A interpreter included in the library. Some embodiments implement genetic operators by using the bytecode form as the genotype for GP. For example, a mutation operator simply replaces a randomly-selected unsigned integer in the bytecode with a new randomly-chosen unsigned integer in the appropriate numeric range (determined by the number of instructions in the instruction set, which is configurable). The interpreter silently ignores errors like division by zero, or indexing outside the valid memory range, but statistics on such events are tracked, which allows us to define custom conditions for determining if a program is trivial.

The relevant Slash/A configuration parameters that are common to all GP instances are as follows:

The number of numeric literals is 16. Some embodiments use a subset of the default instruction set that does not include looping or advanced math (e.g., trigonometric functions). Some embodiments use the following C++ code to generate a new instance of the instruction set.

```
SlashA::InstructionSet* NewInstructionSet( ) {
    SlashA::InstructionSet* iset_ptr = new SlashA::InstructionSet(16);
    iset_ptr->insert_DIS_IO( );       // input/output commands
    iset_ptr->insert_DIS_memreg( );   // memory-register commands
    iset_ptr->insert_DIS_regreg( );   // register-register commands
    iset_ptr->insert_DIS_basicmath( ); // basic math (plus, minus,
    times, divide)
    iset_ptr->insert_DIS_misc( );     // the do-nothing instruction "nop"
    return iset_ptr;
}
```

The length of the data vector used for memory commands is 10.

The programs have a fixed length of 100 instructions.

A program is considered to be trivial, and therefore assigned the lowest fitness score, if either the program does not produce any output, or if the program does not read any input before producing output.

The following genetic operators are also common to all GP instances, in accordance with some embodiments:
1. Use a one-point crossover operator at a rate of 0.5.
2. Use a permutation operator at a rate of 0.012 operating genotype-wise. That is, for each offspring, with a probability of 0.012, its genes are randomly permuted.
3. Use a mutation operator at a rate of 0.004 operating gene-wise. That is, for each gene of each offspring, with a probability of 0.004, the allele is changed to a different allele.

Some embodiments use the convention that the output value r of a program is the first value added to the output buffer, and subsequent values are ignored. Some embodiments map r to a bit value b by setting b=1 if r>0, and b=0 otherwise.

Example Phase 1: Creating Generic Building Blocks

The GP instance for the process is set up as follows.
1. The population size is 1,024.
2. Use t=32 for the number of input-output pairs in the randomized target D. In some embodiments, the data elements in D are generated using the Gaussian and Bernoulli distributions as described above.
3. To assign a fitness score F to a non-trivial program g in the current population, some embodiments first compute the differential fitness d, given the target dataset D, as follows:
Initialize a real variable r to 0.
For each (X, y) in D do the following:
 Run program g on input X.
 If g produces output y, then add 1 to r.
 Else subtract 1 from r.
Let d=absolute_value(r)/t
This gives d a value between 0 and 1. The fitness score is F=1+&d, where e is the selection strength, which has a constant value of 0.5. The motivation for computing fitness this way is that it fulfills two central requirements for a randomized target system:
 a. When F is viewed as a discrete random variable, it should have the same mean and variance for every non-trivial program.
 b. The function encoded by the program should always be assigned the same fitness score as its inverse function, if such a function exists. In this instance, the inverse exists, since another program can output 1 whenever the original outputs 0, and vice versa.
4. Use 32 for the number of test inputs used to generate function signatures.
5. Use 0.5 for the selection strength.
6. Use 0.0625 for the probability of selecting a parent from the seed list rather than the current population.
7. Terminate the process when 200,000 seeds are found.

The process is iterative, and, in some instances produces several hundred programs for each generation. For example, iterating the process 3,498 times (i.e., 3,498 generations) produces 200,000 seeds.

Example Phase 2: Learning Numerical Relations

For the test suite, some embodiments use two GP instances that are designed to learn specific numerical relations, each with three inputs. For GP instance A, a given input sequence $X=(x_1, x_2, x_3)$ is in the relation if it is strictly increasing, i.e., it satisfies the condition $x_1<x_2<x_3$ In some embodiments, GP instance B uses the following condition to determine if X is in its relation: $x_1^2+x_2^2>x_3^2$.

Some embodiments use the Gaussian and Bernoulli distributions (described above) to randomly generate training and test datasets having approximately equal numbers of positive and negative instances. Specifically, for each input-output pair (X, y) that must be generated some embodiments do the following:

Generate y.

Repeatedly generate X until its membership in the relation agrees with y.

Both GP instances A and B have the following configuration properties.

With every generation, some embodiments generate a new training dataset D of size t=32 (as described above), and use the new training dataset as the basis for the fitness score for that generation.

To assign a fitness score F to a non-trivial program g in the current population, some embodiments first compute the differential fitness d as follows.

Initialize a real variable r to 0.

For each (X, y) in D do the following:
  Run program g on input X
  If g produces output y, then add 1 to r.
  Else subtract 1 from r.
Compute d=r divided by t.
  This gives d a value between −1 and 1. The fitness score is F=1+εd. where ε is the selection strength, which has a constant value of 0.5.

The population size is 256.

The termination condition is as follows. With every generation, the program g with the largest fitness score (where ties are broken arbitrarily) is scored again, but this time using a newly-generated test dataset of size t. If g gets a perfect score on both training and test datasets, then the process terminates successfully with g being the solution. If no such solution is found within 2,000 generations, then the process terminates as a failure.

In addition, each GP instance has the option of initializing its population either randomly (a random mode of initialization) or using the last 256 seeds produced in Phase 1 (an seed mode of initialization). Some embodiments run each GP instance A and B in each mode a predetermined number of times (e.g., 10 times). In one experiment, the results obtained are as shown below:

GP instance A in random mode produces 6 successes and 4 failures.

GP instance A in seed mode produces 10 successes and 0 failures.

GP instance B in random mode produces 1 success and 9 failures.

GP instance B in seed mode produces 6 successes and 4 failures.

In this way, the process described above in reference to FIG. 2 provides a significant performance improvement (over traditional ways of seeding populations) for these GP instances.

Example Methods for Feature Extraction Using Genetic Programming

A mathematical analysis provides justification for this feature extraction method. A GP system specifies a fixed programming language L, as well as sets I and O giving the possible inputs and outputs, respectively, for programs in L. A population is a collection of genotypes, where each genotype is a program in L. The phenotype corresponding to a genotype g is the function $\Phi_g$: I→O that is encoded by g. An allele is a program fragment occurring at a fixed locus in a program, and a gene is the set of alleles that are possible at a particular locus.

Typically, a GP system also specifies a problem to be solved, and a fitness function that measures how well a given genotype solves the problem. An initial, randomly generated population evolves by selecting the fittest genotypes to be parents, then applying specified genetic operators on parents to produce the offspring that make up the next generation of the population. This process is repeated with the new generation replacing the old one. The population converges to a solution after many generations. This system is referred to as a static target (ST) system.

In a randomized target (RT) system, on the other hand, the fitness target is chosen randomly with each generation of the population. After many generations, rather than converging to a single phenotype, the RT system produces a population with a large variety of distinct phenotypes. The end product of the RT system is the entire collection of programs representing the distinct phenotypes produced over all generations. Programs in the end-product collection are useful for seeding initial populations in GP systems because they tend to contain complex generic building blocks that would otherwise need to be rediscovered with each new GP instance. Using the techniques described herein, the programs in the end-product collection can also be used as a set of features for the input set I. Thus, the RT system can be used to perform feature extraction, according to some embodiments.

According to some embodiments, at a high-level, the process flow of the RT system is as follows.

1. Initialize the population with randomly generated genotypes.
2. Randomly generate a fitness target (x, y)∈I×O.
3. For each genotype g in the population, compute the fitness score $F_g \in R$ based on how well the value of $\Phi_g(x)$ agrees with y.
4. Select parents from the population using a probabilistic method that favors programs with high fitness such as fitness proportionate selection or tournament selection.
5. Apply genetic operators to the parents to produce the offspring that make up the next generation of the population.
6. Replace the current generation with the next generation of the population.
7. Go to Step 2.

If both weak selection and sexual recombination of genotypes are present, as they are in nature, then evolution is accurately described by a process in linkage equilibrium. In other words, the population can be modeled as if the frequency of any genotype g is just the product of the frequencies of the alleles in g. This result holds under a wide range of assumptions on how fitness is measured and how genotypes recombine. The fitness of a genotype is allowed to be generation-dependent, as is the case here, and sexual recombination may be implemented by almost any form of crossover operator typically used in a GP system.

The weak selection assumption requires that the fitness of all genotypes are close to one another, say within the interval [1 ε, 1+ε], and so the fitness of genotype g can be written as $F_g=1+\varepsilon\Delta_g$, where is the selection strength, assumed to be small, and $\Delta_g \in [-1, 1]$ is called the differential fitness of the genotype. These requirements are easily satisfied by defining $\Delta_g$ to be what one would normally consider to be the fitness score; for example, $\Delta_g=-1$ means that g provides the worst possible match for the fitness target, and $\Delta_g=1$ means that g provides the best possible match.

Consider a machine learning context where the input set I is a training dataset (unlabeled) for a machine learning model. Suppose $I \subset R^n$, where R is the set of all real numbers. From the perspective of machine learning, n is the input dimension. A goal of feature extraction is to find a finite sequence of computable functions $f_1, \ldots f_k: I \rightarrow R$ (each function maps an input $x \in I$ to a real number) that achieves the following objectives as closely as possible.

Every distinct pair $f_i$, $f_j$ is uncorrelated.

k is as large as possible while still being less than n.

This effectively reduces the input dimension from n to k because the sequence of functions can be regarded as a single transformation $T: I \rightarrow R^k$ that removes redundancy while preserving information content, where $T(x)=(f_1(x), \ldots, f_k(x))$ for all $x \in I$. The functions $f_1, \ldots, f_k$ are the features of I.

The techniques described herein differs fundamentally from that of conventional techniques on feature extraction using GP in two major respects. First, the techniques can be used for unsupervised learning. Second, rather than relying on a complex fitness function to find good features, it relies on an interesting property of evolution itself: when the target is randomized, evolution naturally produces features of the input dataset. This results in a more efficient process since the fitness function is far less complex. Currently, the most popular method for automated feature extraction in an unsupervised setting is principal component analysis, but this is a form of linear projection, which limits the complexity of the possible features that can be produced. On the other hand, the techniques described herein allow any computable function to be a feature, limited only by available computational resources. Furthermore, the features can be described in terms of the programming language of our choice, potentially making features more explainable.

Some embodiments model the fitness of a genotype g by the discrete random variable $X_g: I \times O \rightarrow R$ that maps the fitness target (x, y) to the fitness score $F_g$. $X_g$ is called a genotype variable. As the following examples demonstrate, every genotype variable has the same mean, equal to 1, and the same variance, hereafter denoted by $\sigma_0^2$.

Example RT System 1

Some embodiments model an RT system with $I=\{0, 1\}^n$ and $O=\{0, 1\}^m$ for fixed positive integers m and n. Some embodiments use a uniform probability distribution on the sample space $I \times O$ so that each possible pair (x, y) is equally likely. For a given genotype g, some embodiments compute the differential fitness $\Delta_g \in [-1, 1]$ for a randomly chosen fitness target (x, y) by the following pseudocode.

1. Let $z=\Phi_g(x)$ and d=0.
2. For every bit position i between 1 and m, if bit $z_i$ agrees with $y_i$, then add 1 to d, else subtract 1 from d.
3. Let $\Delta_g=d/m$.

Step 2 above is equivalent to a one-dimensional random walk with d being the final position relative to the origin after m steps. Since d has the same mean and variance for all g, with the mean being 0, it follows that $X_g$ has the same mean and variance for all g, with the mean being 1.

Example RT System 2

For a more generic RT system, some embodiments use input and output bit sequences of arbitrary length, $I=O=\{0, 1\}^*$, which can encode any conceivable information. Some embodiments use a variant of the uniform probability density function shown below.

$$p(x)=2^{-2l(x)-1}$$

In the equation above, x is any bit sequence of length l(x). Some embodiments select random values for x from the set $\{0,1\}^*$ using this density function as follows.

1. Let x be an empty bit sequence.
2. Randomly choose a bit b with 0 and 1 equally likely.
3. If b=0, then use the current value of x as the final choice.
4. Else append to x a randomly chosen bit with 0 and 1 equally likely, and go to Step 2.

The computation of $\Delta_g$ for a given genotype g and fitness target (x, y) is the same as that of the previous Example RT System, except that the length of z is first coerced to be the same as that of y by appending zeros to z if its length is less, or by truncating z if its length is greater. This again leads to a random walk with the number of steps equal to the length of y, and not dependent on g, so every $X_g$ has the same mean and variance, with the mean being 1.

The RT system implements weak selection and sexual recombination, therefore the frequency of an allele changes over time as described by the following equation:

$$p_{ij}^{t+1}=(F_{ij}^t/W^t) \cdot p_{ij}^t \qquad (1)$$

In the equation above, $p_{ij}^t$ is the frequency of allele j of locus i in the population at generation t, $F_{ij}^t$ is the mean fitness at generation t over all genotypes that contain allele j at locus i, and $W^t$ is a normalizing constant designed to keep the frequencies summing to 1 at generation t.

For every allele j of locus i and generation t, an allele variable $X_{ij}^t: I \times O \rightarrow R$ is defined to be the discrete random variable that maps the fitness target (x, y) to the allele's mean fitness $F_{ij}^t$. Then $X_{ij}^t$ can be expressed as the average of all $X_g$ such that genotype g is present in generation t and contains allele j at locus i. $X_{ij}^t$ is linked to every such $X_g$. All allele variables have a mean of 1, but their variances may differ.

Suppose j and k are two distinct alleles of the same locus i. Equation (1) above favors allele j over allele k during the time period from some generation $t_1$ to a later generation $t_2$ if the following inequality is true.

$$\Pi_{t=t_1}^{t_2} F_{ij}^t > \Pi_{t=t_1}^{t_2} F_{ik}^t \qquad (2)$$

Some embodiments achieve the inequality above in a probabilistic sense by making the variance of $X_{ij}^t$ less than that of $X_{ik}^t$ for every generation t between $t_1$ and $t_2$. To see the justification for this, define product variables by the equations $Y_j = \Pi_{t=t_1}^{t_2} X_{ij}^t$ and $Y_k = \Pi_{t=t_1}^{t_2} X_{ik}^t$.

From the fact that every generation makes an independent choice of fitness target, it follows that any two allele variables from different generations are statistically independent. In this case, the mean of the product is the product of the means, so both product variables have a mean of 1, which might lead one to believe that the two are indistinguishable. However, as the following example shows, the distribution of a product variable becomes more heavily skewed towards low values as the variance of each of its constituent allele variables increases.

Example RT System 3

Figure 3:
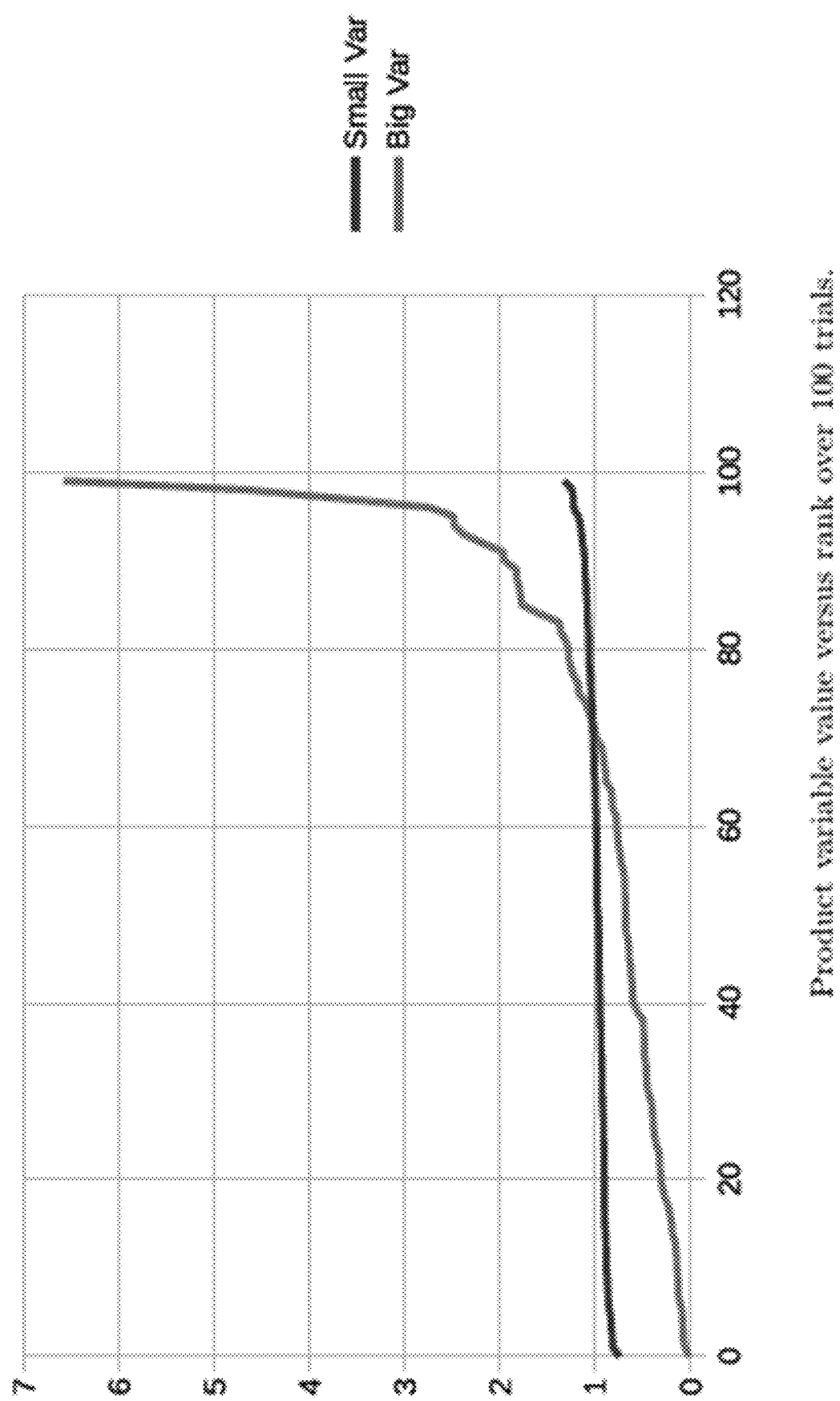
FIG. 3 illustrates a graph plot of the product variable versus rank over several trials, according to some embodiments.

A C++ program ran 100 trials of an experiment that simulates two product variables over 100 generations. FIG. 3 illustrates a plot of the product variable versus rank over the 100 trials, according to some embodiments. The product variable labeled "Small Var" simulates constituent allele variables with small variance, and the other product variable labeled "Big Var" simulates constituents with big variance. The output is formatted as a spreadsheet, which is graphed in FIG. 3. The graph in FIG. 3 shows that the small variance product variable ends up with a larger value than the big variance product variable in roughly two-thirds of the trials. This leads to the conclusion that an RT system generally favors alleles with small variance in mean fitness over those with large variance.

Express the variance of a typical allele variable $X_{ij}^t$ in terms of its linked genotype variables $X_{g_1}, X_{g_2}, \ldots, X_{g_s}$.

$$\text{Var}(X_{ij}^t) = \text{Var}\left(\frac{1}{s}\sum_{a=1}^{s} X_{g_a}\right) = \frac{\sigma_0^2}{s} + \left(\frac{2}{s^2}\right)\sum_{a=1}^{s-1}\sum_{b=a+1}^{s} \text{Cov}(X_{g_a}, X_{g_b}) \quad (3)$$

Because $\sigma_0^2$ is a constant of the RT system, the right side of Equation (3) is minimized when the allele in question has numerous linked genotypes, with as many pairs of them as possible having covariance that is zero or negative. Zero covariance means the pair is uncorrelated, and negative covariance means the pair is anti-correlated. Either situation implies that the phenotypes behave very differently from each other.

Example RT System 4

Another C++ program repeated 100 trials of an experiment that runs a simple RT system over 500 generations.

A genotype in this example system is a sequence of r+1 bits, where each bit is a gene with alleles 0 and 1. The first gene is a master control that determines how the remaining r genes are used in the function $\Phi$ that is encoded, which takes as input a sequence of $2^r$ bits and produces a single bit as output. Allele 0 of the control gene ignores the remaining genes and defines $\Phi$ to be the function that returns 0 for every input, whereas allele 1 interprets the r bits of the remaining genes as an unsigned integer representing a position in the input sequence, and $\Phi$ returns the value of the input bit in that position as its output.

Allele 0 of the control gene can only be linked to a single phenotype in any population. Any pair of genotypes linked to allele 0 has positive covariance. But allele 1 is likely to be linked to many distinct phenotypes, with many pairs being uncorrelated, meaning they have zero covariance. In this way, evolution favors allele 1 over allele 0.

At the end of each trial, the final frequency of allele 1 as a percent is recorded. The data is formatted as a spreadsheet giving the final frequency of allele 1 versus rank in descending order, which is graphed in FIG. 4, according to some embodiments. Allele 1 is indeed favored in most trials. In fact, about two-thirds of the time, allele 1 ends the trial with a frequency of 80% or better.

The quantity expressed in Equation 3 is the variance of the allele in question. In order to achieve the goal of using programs in the end-product collection of an RT system as the features of the input dataset, some embodiments seek low allele variance to correspond to many uncorrelated functions among the allele's linked phenotypes. Unfortunately, it's possible for the system to have a single allele linked to every member of a large population, where the allele has the minimum possible variance of zero, and yet there are only two phenotypes in total, which are anti-correlated rather than uncorrelated. This can happen if the two phenotypes are inverses of each other, so their covariance has the minimum possible value of $-\sigma_0^2$, and the population has an even number of members, with half being one phenotype and half being the other.

Although this situation is not possible in the Example RT System 4 described above (because the programming language is not expressive enough for inverses to exist), for successful feature extraction, the programming language should be very expressive.

Some embodiments solve the problem described above by modifying the fitness function so that it gives every phenotype the same score as its inverse while leaving the relative scores of non-inverse pairs about the same. In some embodiments, in the modified fitness function: (i) pairs of phenotypes that were previously highly anti-correlated become highly correlated, (ii) pairs that were highly correlated remain highly correlated, and (iii) pairs that were highly uncorrelated remain highly uncorrelated. Thus, after the change, the most likely way for allele variance to be low is for many pairs of linked phenotypes to be highly uncorrelated, which is appropriate for feature extraction.

Some embodiments, as described above in reference to Example RT Systems 1 and 2, identify the differential fitness value with the position relative to the origin at the end of a one-dimensional random walk based on comparing the target output with the actual output. Some embodiments use the distance from the origin, which is always non-negative, instead of the position, which may be positive, negative or zero. This gives inverses the same score as each other, but if the random walk is not long enough, then the ability to distinguish between non-inverses is lost. In the worst case, when the output is only a single bit, every phenotype is assigned the same score. To address this issue, some embodiments change the randomized target (x, y) into a reasonably large fixed-size sequence of random input-output pairs $((x_1, y_1), \ldots, (x_u, y_u))$, and the random walk occurs on the entire sequence of outputs. As required, this results in inverses getting the same score, while non-inverses have essentially the same relationship as before. The mean of a genotype variable is no longer exactly 1, but it is still the case that every genotype variable has the same mean and variance, thus satisfying the requirements for feature extraction.

Example RT System for Feature Extraction

This section describes other characteristics of the RT system to implement feature extraction, according to some embodiments. It is desirable for the programming language L to be Turing complete so that any computable phenotype is possible in theory. Some embodiments weigh this against the fact that any implementation has limits on computational resources, most notably memory space and processor speed. In some embodiments, the RT system can produce an ever-increasing variety of phenotypes as resources are scaled up.

Examples for Suppressing Errors

A randomly generated program in a Turing complete programming language is likely to produce behavior that would be considered an error if written by a human programmer, such as halting without producing output, or exceeding resource limits. In order to suppress this behavior in an RT system, some embodiments modify the fitness function so that it detects any such error in a program and assigns it the lowest possible score in that case.

This modification violates the assumption given earlier that every genotype has the same mean fitness, but it does not affect the conclusion that a choice between two alleles with the same mean fitness favors the allele with the lower variance in mean fitness over time.

Example Methods for Preserving Phenotypes

Figure 4:
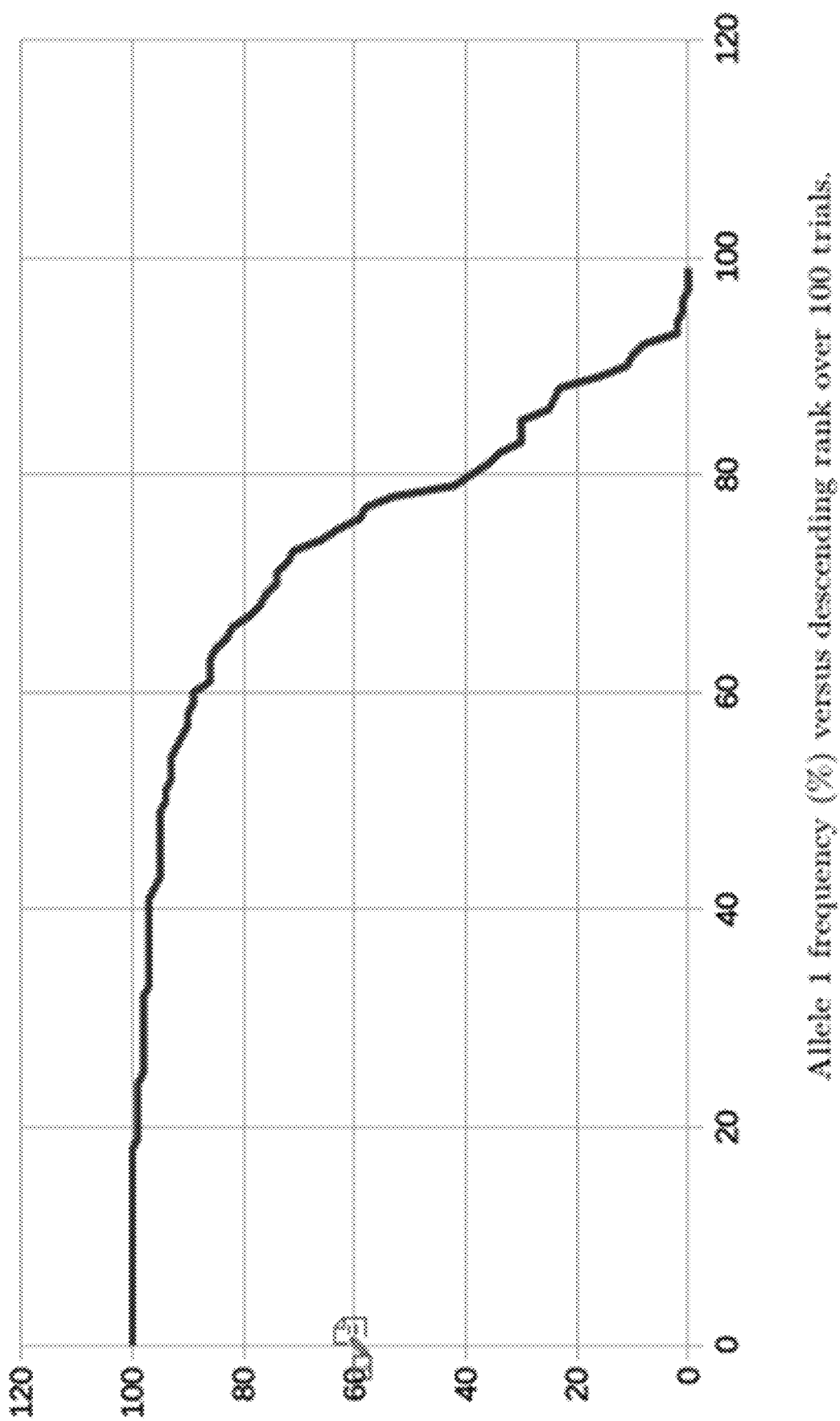
FIG. 4 illustrates a graph plot of final frequency of allele 1 versus rank in descending order, according to some embodiments.

Some embodiments optimize situations shown in the right side of the graph in FIG. 3 and the right side of the graph in FIG. 4. During any span of generations, there is the distinct possibility that a bad allele, linked to very few phenotypes, defeats a good allele, linked to many phenotypes. This doesn't often happen, but when it does, it tends to be a decisive victory for the bad allele. What this means for feature extraction is that, over any sufficiently long number of generations, there is a mass extinction event in which a large variety of phenotypes disappears from the population. Assuming the system uses a mutation operator, the damage can eventually be repaired, but this means starting over from scratch. As a practical matter, some embodiments provide a faster way to recover from extinction events, as described below.

Some embodiments catalog and preserve new phenotypes as they are discovered. This has the added benefit of allowing the system's progress to be tracked in terms of the number of phenotypes produced. A straightforward implementation is as follows. During initialization of the system, some embodiments randomly generate a sequence of test inputs $(x_1, x_2, \ldots, x_v) \in I^v$, which remains fixed for the lifetime of the system. With every generation and every genotype g in the population, compute the signature of the phenotype $\Phi_g$, which is defined to be the sequence of outputs $(\Phi_g(x_1), \Phi_g(x_2), \ldots, \Phi_g(x_v)) \in O^v$. The phenotype is considered to be new if its signature has not been seen before, in which case g is stored in a persistent table keyed by the signature of $\Phi_g$. Besides using this table to determine when a signature is new, some embodiments use it as an archive of all known phenotypes.

Rather than attempting to determine when a mass extinction has occurred and then restoring phenotypes to the population from the archive, it is simpler, yet very effective, to mix a small random sample from the archive into the population with every generation. Specifically, each time a parent for the next generation is to be selected, with a small probability $p_0$, some embodiments select the parent at random from the archive instead of selecting from the current generation of the population. This gives a continuous added advantage to good alleles since they tend to be more highly represented in the archive than bad alleles.

In conventional GP systems that use a phenotype archive, it is not enough for a phenotype to be new in order to qualify for addition to the archive. Instead, the amount by which the phenotype differs from previous ones is measured, and it must exceed some threshold to qualify. In such systems, the use of an archive is essential for achieving phenotypic diversity. On the other hand, an RT system uses the more efficient approach of relying on the mechanics of evolution itself to measure phenotypic diversity, as expressed in Equation 3. The fact that an RT system tends to produce phenotypic diversity even without the use of an archive is demonstrated in the Example RT System 4 described above, according to some embodiments.

Example End Product

In some embodiments, the phenotype archive described above is the basis for the end product of the RT system. To produce the end product, some embodiments select a particular subset of size w from the phenotype archive depending on the goal, with w being the desired number of programs.

In some embodiments, to produce generic building blocks for seeding GP instances, the phenotype archive is also known as the seed list, and the programs on the list are called seeds. For the end product, some embodiments select the w seeds that were most recently added to the list, where w is the desired population size for the GP instance to be seeded. This method is sometimes called the recent-seed selection method.

For feature extraction, some embodiments view the phenotype archive as a list of candidates for features, and use one or more well-established feature-selection techniques that can be applied to select the w best candidates as the extracted features. In machine learning, feature selection is normally applied to the list of input data elements as a means of reducing input dimension (an alternative to feature extraction). Instead, some embodiments apply it here to the list of feature candidates as the final step in the feature-extraction process. Some feature-selection techniques are appropriate for unsupervised learning, and some are strictly for supervised learning, meaning that they require labeled input data.

In the case of unsupervised learning, where the input data is unlabeled, feature selection typically favors candidates with large standard deviation in their output values so that data points are easier to distinguish from each other. Some embodiments combine this with the requirement that pairs of features should be highly uncorrelated. A simple but effective approach is to first sort the list of candidates in descending order of standard deviation to produce a list S. Next, compute a correlation score for each candidate c on list S, which is the maximum absolute value of the correlation of c with any other candidate preceding c on list S. Finally, sort S in ascending order of correlation score to produce list R, and use the first w candidates on R as the extracted features. This method is sometimes called the maximum-standard-deviation-minimum-correlation selection method.

In some embodiments, if the input data is labeled, to use the labels for feature extraction, the candidates that are highly correlated (positively or negatively) with one or more labels are favored. This is particularly appropriate if there is only one type of label, and/or to determine how the data relates to that label. The simplest approach for this relaxes the requirement that pairs of features be uncorrelated. Some embodiments simply sort the list of candidates in descending order of absolute value of correlation with the label, and use the first w candidates on the sorted list. Conveniently, the fact that each candidate has a distinct phenotype ensures that there are no duplicates among the extracted features. This method is sometimes called the maximum-correlation selection method. This method is also appropriate for generic building block creation for evolving a model for one particular label.

Generic Building Blocks for Features

Some embodiments improve the performance of the feature extraction process, both in terms of computational resources expended and quality of the result obtained, by using generic-building-block creation to seed the initial population rather than seeding randomly.

This is certainly true if the goal is to perform feature extraction on multiple datasets within the same problem domain. For example, many of the building blocks that are useful for features of images of handwritten digits are also useful for features of images of handwritten alphabetic characters, especially if the images have the same size and shape in each case. Some embodiments save on computational resources by creating the generic building blocks first and then reusing them for both cases.

Some embodiments use generic building blocks even with only one dataset. This technique allows the initial population to contain a complex variety of phenotypes that might be hard to produce using only the measured data as input. This technique also helps to find complex features that might be more appropriate than simpler ones.

Example Use Cases

This section describes use cases that demonstrate successful feature extraction using the techniques described here and above, in two diverse settings: image classification and disease prediction based on measured health data. Each case uses a distinct programming language that is appropriate for the problem domain. Labeled data that is partitioned into training and test datasets is available for both cases. In some embodiments, when the features are extracted, the data is treated as unlabeled in the case of image classification in order to demonstrate unsupervised learning. In some embodiments, when the features are extracted, the data is treated as labeled for disease prediction to show supervised learning. The general approach that is common to both cases is as follows.

Some embodiments use a first RT system to create generic building blocks for features of the problem domain in question, and use a second RT system that leverages the generic building blocks to extract features of the training dataset. Some embodiments use the extracted features, to transform input data in both training and test datasets to bit sequences with reduced input dimension, as described above.

Some embodiments train a standard classifier on the transformed training dataset, and determine effectiveness of the classifier on the transformed test dataset. Some embodiments produce a shallow (no hidden layers), fully connected artificial neural network (ANN) as the classifier, having one output node for each label (or class), and using the activation function sigmoid. Some embodiments set 0.04 as the desired mean squared error (MSE) for training. Experiments show that embodiments of the techniques described herein achieve the desired error on both the training and test datasets.

Experiments showed the above performance is comparable to that of a similarly configured shallow ANN trained on the original training dataset and tested on the original test dataset. The former ANN performed as well as the latter thereby showing that the input dimension has been reduced without loss of information content, as required for successful feature extraction.

Example Use Case 1: Classifying Handwritten Digits

Some embodiments use the MNIST database, which contains tens of thousands of scanned images of handwritten digits, together with their correct classifications. The database is divided into training and test datasets, with 60,000 and 10,000 images, respectively. The images are grayscale and 28 by 28 pixels in size.

Example Setup

Some embodiments set up the RT systems as follows:
1. Reformat all images so that each pixel value, which originally ranges from 0 to 255, is translated to a single bit, with 0 corresponding to the interval [0, 127] and 1 corresponding to [128, 255]. For creation of generic building blocks, let $I=\{0, 1\}^n$, where the input dimension is $n=28\times28=784$. For feature extraction, I is the subset of $\{0, 1\}^n$ corresponding to the training dataset.
2. For both RT systems, let $O=\{0, 1\}$.
3. For both RT systems, let the probability distribution of the randomized target be uniform on the sample space $I\times O$.
4. For the programming language L of both RT systems, use the language of Perceptron Turing Machines (PTMs). This language is Turing complete and allows for a form of neuro-evolution, meaning that each program generates an ANN. The relevant PTM configuration parameters are as follows.
   a. The number of states is 512.
   b. The number of tapes is 2, with each tape having a length of 5 bits, which is long enough to contain either a row index or a column index of an input image. Both tapes are input index tapes, and there are no output index tapes since the output is a single bit.
   c. Every program has a fixed length of 4,096 instructions.
   d. Set resource limits on the ANN generated by a program as follows:
      i. The maximum number of nodes is 50,000.
      ii. The maximum depth is 100.
      iii. The maximum fanout is 16.
      iv. If a resource limit is exceeded, it is considered to be an error, in which case the program is assigned the lowest possible fitness score.
5. Set the population size to 1,024 for both RT systems.
6. Terminate generic building block creation when at least 100,000 seeds are produced, and terminate feature extraction when at least 100,000 candidates are produced.
7. For the end-product selection methods, use recent-seed with a size (parameter w) of 1,024 for generic building block creation, and use maximum-standard-deviation-minimum-correlation with a size of 300 for feature extraction.
8. Use 32 for the number of input-output pairs in the randomized target.
9. Use 32 for the number of test inputs used to generate phenotype signatures.
10. Use 0.5 for the selection strength.
11. Use 0.0625 for the probability of selecting a parent from the phenotype archive.
12. Define genetic operators as follows.
    a. Use uniform crossover at a rate of 0.5 operating on a gene-by-gene basis.
    b. Use a permutation operator at a rate of 0.003 operating genotype-wise. That is, for each offspring, with a probability of 0.003, its genes are randomly permuted.
    c. Use a mutation operator at a rate of 0.001 operating gene-wise. That is, for each gene of each offspring, with a probability of 0.001, the allele is changed to a different allele.

Example Results

The first RT system produces 100,000 seeds, and the most recently produced 1,024 seeds serve as the initial population of the second RT system. The second RT system produces 300 extracted features, which transform the training and test datasets in order to reduce the input dimension from 784 to 300. Running the ANN on the transformed datasets produces the following output.

```
Max epochs    1000. Desired error: 0.0399999991.
Epochs           1. Current error: 0.3200925291. Bit fail 335963.
Epochs          10. Current error: 0.0488955826. Bit fail 36353.
Epochs          17. Current error: 0.0389786735. Bit fail 29433.
```

On test data, MSE: 0.038661, bit fail: 4924.

Compare this to running the ANN on the original datasets, with output as follows.

```
Max epochs    1000. Desired error: 0.0399999991.
Epochs           1. Current error: 0.3162646294. Bit fail 310092.
Epochs          10. Current error: 0.0951004773. Bit fail 70813.
Epochs          14. Current error: 0.0325109586. Bit fail 24349.
```

On test data, MSE: 0.034387, bit fail: 4418.

As shown above, the ANN using extracted features has performance that is comparable to that of the ANN using original datasets, which demonstrates successful feature extraction.

Example Use Case 2: Predicting Heart Disease

Some embodiments use a publicly-available dataset containing 13 measured health attributes for each of 303 anonymous patients, together with an indication of whether the patient has heart disease (1=yes, 0=no), which is used as a label (or target class). As a preliminary step, some embodiments randomly partition the data into a training dataset representing 242 patients and a test dataset representing 61 patients.

Example Setup

Some embodiments set up the RT systems as follows.
1. Normalize each of the 13 input data elements based on the mean and standard deviation from the training dataset. That is, for each input $x_i$, where $1 \leq i \leq 13$, let $\mu_i$ be the mean and let $\sigma_i$ be the standard deviation of $x_i$, and replace $x_i$ with its normalized value $x_i^{norm}$ given by the following equation.

$$x_i^{norm} = \frac{x_i - \mu_i}{\sigma_i},$$

if $\sigma_i$ is not equal to 0, and, 0, otherwise.
   For creation of generic building blocks, let $I=R^n$, where the input dimension is n=13. For feature extraction, I is the subset of corresponding to the training dataset (after normalization).
2. For both RT systems, let O={0, 1}.
3. For creation of generic building blocks, the probability distribution of the randomized target is equivalent to independently choosing each input data element $x_i$ according to a Gaussian distribution with mean 0 and standard deviation 1, and independently choosing the output according to the uniform distribution on O. The Gaussian distribution $\varphi(x_i)$ is given by the following equation.

$$\varphi(x_i) = 1/\text{sqrt}(2\pi)e^{-\left(\frac{1}{2}\right)x_i^2}$$

Then, for $(x, y) \in I \times O$, with $x=(x_1, \ldots, x_n)$, the probability distribution is given by the following equation.

$$p(x, y) = \left(\frac{1}{2}\right)\prod_{i=1}^{n}\varphi(x_i)$$

For feature extraction, the probability distribution of the randomized target is the uniform distribution on the sample space I×O.
4. The programming language L is Slash/A as developed by Artur B Adib. This is a Turing complete imperative programming language that is ideal for analyzing numerical datasets because all inputs and outputs are real numbers in double precision floating-point form. The following example reads two in-puts, adds them together, and returns the result as an output.

```
input/     # get the next number from the input buffer and save it to
           register F
0/         # set register I = 0
save/      # save content of F into data vector D[I] (i.e. D[0] := F)
input/     # get another input, save to F
add/       # add to F current data pointed to by I (i.e. F := F + D[0])
output/.         # append F to the output buffer
```

Slash/A is implemented as a C++ library, which includes a function for transforming a program given in text form as above into bytecode form, which is simply an array of unsigned integers, with each unsigned integer mapping to a unique instruction in the language. It is the bytecode form that is used by the Slash/A interpreter included in the library. By using the bytecode form as the genotype for GP, genetic operators become easy to implement. For example, a mutation operator simply replaces a randomly-selected unsigned integer in the bytecode with a new randomly-chosen unsigned integer in the appropriate numeric range (determined by the number of instructions in the instruction set, which is configurable). The interpreter ignores errors like division by zero, or indexing outside the valid memory range, but statistics on such events are tracked, which allows the system to define custom conditions for determining if a program is trivial.
The relevant Slash/A configuration parameters that are common to both RT systems are as follows, according to some embodiments.
a) Use 2 numeric literals, and use a subset of the default instruction set that does not include looping or advanced math (e.g., trigonometric functions). Some embodiments use the following C++ code to generate a new instance of the instruction set.

```
SlashA::InstructionSet* NewInstructionSet( ) {
    SlashA::InstructionSet* iset_ptr = new SlashA::InstructionSet(2);
    iset_ptr->insert_DIS_IO( );           // input/output commands
    iset_ptr->insert_DIS_memreg( );       // memory-register commands
    iset_ptr->insert_DIS_regreg( );       // register-register commands
    iset_ptr>insert_DIS_basicmath( );     // basic math (plus, minus,
                                          times,
                                          // divide)
    iset_ptr->insert_DIS_misc( );         // the do-nothing instruction
                                          // "nop"
    return iset_ptr;
}
``` b) The length of the data vector used for memory commands is 100.
c) Every program has a fixed length of 128 instructions.
d) Some embodiments consider a program to be trivial, and therefore assign the lowest fitness score, if:
  i. the program does not produce any output;
  ii. the program does not read any input before producing output;
  iii. the program produces an output that is a NaN or an INFINITY according to the IEEE Standard for Floating-Point Arithmetic.
e) Use the convention that the output value r of a program is the first value added to the output buffer, and subsequent values are ignored. Some embodiments map r to a bit value b by setting b=1 if r>0, and b=0 otherwise.
5. Set the population size to 1,024 for both RT systems.
6. Terminate generic building block creation when at least 100,000 seeds are produced, and terminate feature extraction when at least 100,000 candidates are produced.
7. For the end-product selection methods, use recent-seed with a size (parameter w) of 1,024 for generic building block creation, and use maximum-correlation with a size of 6 for feature ex-traction.
8. Use 32 for the number of input-output pairs in the randomized target.
9. Use 32 for the number of test inputs used to generate phenotype signatures.
10. Use 0.5 for the selection strength.
11. Use 0.0625 for the probability of selecting a parent from the phenotype archive.
12. Define genetic operators as follows.
  a. Use a one-point crossover operator at a rate of 0.5.
  b. Use a permutation operator at a rate of 0.003 operating genotype-wise. That is, for each offspring, with a probability of 0.003, its genes are randomly permuted
  c. Use a mutation operator at a rate of 0.001 operating gene-wise. That is, for each gene of each offspring, with a probability of 0.001, the allele is changed to a different allele.

Example Results

The first RT system produced 100,000 seeds, and the most recently produced 1,024 seeds serve as the initial population of the second RT system. The second RT system produced 6 extracted features, which transform the training and test datasets in order to reduce the input dimension from 13 to 6. Running the ANN on the transformed datasets produced the following output.

| Max epochs | 1000. | Desired error: 0.0399999991. |
|---|---|---|
| Epochs | 1. | Current error: 0.2840425670. Bit fail 205. |
| Epochs | 100. | Current error: 0.1104911044. Bit fail 36. |
| Epochs | 200. | Current error: 0.1104902178. Bit fail 36. |
| Epochs | 300. | Current error: 0.1104939356. Bit fail 36. |
| Epochs | 400. | Current error: 0.1104927137. Bit fail 36. |
| Epochs | 500. | Current error: 0.1104928628. Bit fail 36. |
| Epochs | 600. | Current error: 0.1104914248. Bit fail 36. |
| Epochs | 700. | Current error: 0.1104924232. Bit fail 36. |
| Epochs | 800. | Current error: 0.1104900017. Bit fail 36. |
| Epochs | 900. | Current error: 0.1104932278. Bit fail 36. |
| Epochs | 1000. | Current error: 0.1104911566. Bit fail 36. |

On test data, MSE: 0.128879, bit fail: 11.

Compare this to running FANN on the original datasets, with output as follows.

| Max epochs | 1000. | Desired error: 0.0399999991. |
|---|---|---|
| Epochs | 1. | Current error: 0.2501831055. Bit fail 129. |
| Epochs | 100. | Current error: 0.1037608609. Bit fail 35. |
| Epochs | 200. | Current error: 0.1037616581. Bit fail 35. |
| Epochs | 300. | Current error: 0.1037597805. Bit fail 35. |
| Epochs | 400. | Current error: 0.1037595570. Bit fail 35. |
| Epochs | 500. | Current error: 0.1037613377. Bit fail 35. |
| Epochs | 600. | Current error: 0.1037596688. Bit fail 35. |
| Epochs | 700. | Current error: 0.1037595049. Bit fail 35. |
| Epochs | 800. | Current error: 0.1037632823. Bit fail 35. |
| Epochs | 900. | Current error: 0.1037593707. Bit fail 35. |
| Epochs | 1000. | Current error: 0.1037603393. Bit fail 35. |

On test data, MSE: 0.138724, bit fail: 16.

As shown above, the ANN using extracted features has performance that is comparable to that of the ANN using original datasets, which demonstrates successful feature extraction.

In this way, the evolution in the presence of a randomized target produces features of the input dataset, and can be used to provide an efficient, generic method for automated feature extraction. Thus, the system can be used for unsupervised learning, can produce features of arbitrary complexity, and its features can be expressed in any programming language of choice.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of evolving generic computational building blocks, the method comprising:
    initializing a parent population with programs that encode functions by either (i) randomly generating the programs or (ii) using programs evolved by a genetic programming instance that uses randomized targets;
    obtaining a list of randomly generated test inputs;
    generating a target dataset that includes initial input-output pairs of randomly generated binary strings;
    applying a fitness function to assign a fitness score to each program in the parent population, wherein the fitness score represents at least an ability of a respective program in the parent population to match the initial input-output pairs of the target dataset;
    initializing a seed list with copies of the programs in the parent population that satisfy a novelty condition, wherein the novelty condition is representative of an ability of a program to produce distinct and unique output for the list of randomly generated test inputs;
    determining if a terminating condition of the seed list has been satisfied, wherein the terminating condition is representative of an ability of one or more programs in the seed list to solve one or more genetic programming instances;
    in accordance with a determination that the terminating condition has not been satisfied:
    applying at least one genetic operator to the parent population to obtain a current offspring population of programs, wherein the at least one genetic operator includes operators applied to the parent population to grow the seed list, based on fitness scores of the programs in the parent population, to solve the one or more genetic programming instances; and
    repeating steps of:
        generating a new target dataset that includes new input-output pairs of randomly generated binary strings;
        applying the fitness function to assign a new fitness score to each program in the current offspring population, wherein the new fitness score represents at least an ability of a respective program in the current offspring population to match the new input-output pairs of the new target dataset;
        appending, to the seed list, copies of the programs in the current offspring population that satisfy the novelty condition; and
        applying the at least one genetic operator to the current offspring population to obtain a new offspring population of programs and setting the new offspring population of programs as the current offspring population;
    until said termination condition is satisfied.

2. The method of claim 1 further comprising:
    using the seed list to initialize populations within a test suite of genetic programming instances representing a plurality of problems; and
    determining if the terminating condition has been satisfied based on test results of the test suite.

3. The method of claim 1 further comprising:
    when applying the at least one genetic operator to the current offspring population, selecting, based on a Bernoulli distribution, the programs in the seed list over the programs in the current offspring population, as parents, wherein each program in the seed list is equally likely to be selected as a parent.

4. The method of claim 1, wherein whether a program in the parent population or the current offspring population satisfies the novelty condition is based on:
    a determination that the program in the parent population or the current offspring population encodes a function that generates a sequence of outputs, for the randomly generated test inputs, that is distinct from sequences of outputs generated by functions encoded by the programs in the seed list, for the randomly generated test inputs.

5. The method of claim 4 further comprising:
    determining and storing, for each respective program in the seed list, function signatures that include the sequences of outputs generated by the functions encoded by the respective program in the seed list for the randomly generated test inputs; and
    retrieving the function signatures;
    wherein determination that the respective program in the seed list encodes a function that is distinct from functions encoded by programs in the seed list is further based on:
        a determination that the respective program in the seed list encodes the function that generates a sequence of outputs, for the randomly generated test inputs, that is distinct from the function signatures.

6. The method of claim 1, wherein the terminating condition depends at least on size of the seed list.

7. The method of claim 1, wherein the terminating condition depends at least on a determination if the seed list is growing at a predetermined growth rate.

8. The method of claim 1 further comprising breaking ties arbitrarily when applying the fitness function.

9. The method of claim 1 further comprising discarding programs from the seed list that encode trivial functions that do not read input, when initializing the seed list and appending to the seed list.

10. The method of claim 9 further comprising performing syntactic analysis to identify the programs in the seed list that encode the trivial functions that do not read the input.

11. The method of claim 1 further comprising discarding programs from the seed list that encode functions that have abnormal runtime behavior or have abnormal resource requirements, when initializing the seed list and appending to the seed list.

12. The method of claim 1 further comprising seeding an initial population for a new instance of genetic programing using a predetermined number of programs in the seed list.

13. The method of claim 1, wherein the at least one genetic operator is one or more of a selection operator, a mutation operator, and a crossover operator.

14. The method of claim 1, wherein each input of the randomly generated test inputs and each input of the initial input-output pairs of randomly generated binary strings are generated based on an input probability distribution, and each output of the initial input-output pairs of randomly generated binary strings is generated based on an output probability distribution.

15. The method of claim 14, wherein the input probability distribution is a Gaussian distribution over range of pixel intensities, and the output probability distribution is a Gaussian distribution over [0.0, 1.0].

16. The method of claim 14, wherein the input probability distribution uses a sample space that is based on a training dataset for a machine learning model.

17. The method of claim 16 further comprising extracting features of the training dataset by regarding the seed list as a set of candidate features and applying a feature selection technique to select a subset providing the extracted features.

18. The method of claim 1, wherein the fitness function assigns same fitness score to programs that encode functions that produce bitwise opposite output for same input.

19. The method of claim 1, wherein the fitness function assigns a fitness score between −1 and 1 to a particular program in order to measure a degree of match between an output of the particular program and the target dataset, with larger values denoting higher degree of match.

20. The method of claim 1, wherein the one or more genetic programming instances includes a genetic programming instance for partial classification of handwritten digits, and the initial input-output pairs of randomly generated binary strings and the new input-output pairs of randomly generated binary strings are generated based on images from MNIST database, and the method further comprises terminating the method after iterating 2000 times.

21. A computer system for generating data visualizations comprising:
  one or more processors; and
  memory;
  wherein the memory stores instructions executed by the one or more processors, and the instructions for:
  initializing a parent population with programs that encode functions by either (i) randomly generating the programs or (ii) using programs evolved by a genetic programming instance that uses randomized targets;
  obtaining a list of randomly generated test inputs;
  generating a target dataset that includes initial input-output pairs of randomly generated binary strings;
  applying a fitness function to assign a fitness score to each program in the parent population, wherein the fitness score represents at least an ability of a respective program to match the initial input-output pairs of the target dataset;
  initializing a seed list with copies of the programs in the parent population that satisfy a novelty condition, wherein the novelty condition is representative of an ability of a program to produce distinct and unique output for the list of randomly generated test inputs;
  determining if a terminating condition of the seed list has been satisfied, wherein the terminating condition is representative of an ability of one or more programs in the seed list to solve one or more genetic programming instances;
  in accordance with a determination that the terminating condition has not been satisfied:
    applying at least one genetic operator to the parent population to obtain a current offspring population of programs, wherein the at least one genetic operator includes operators applied to the parent population to grow the seed list, based on fitness scores of the programs in the parent population, to solve the one or more genetic programming instances; and
    repeating steps of:
      generating a new target dataset that includes new input-output pairs of randomly generated binary strings;
      applying the fitness function to assign a new fitness score to each program in the current offspring population, wherein the new fitness score represents at least an ability of a respective program in the current offspring population to match the new input-output pairs of the new target dataset;
      appending, to the seed list, copies of the programs in the current offspring population that satisfy the novelty condition; and
      applying the at least one genetic operator to the current offspring population to obtain a new offspring population of programs and setting the new offspring population of programs as the current offspring population;
    until said termination condition is satisfied.

22. A non-transitory computer readable storage medium storing one or more instructions executed by a computer system having a display, one or more processors, and memory, the instructions for:
  initializing a parent population with programs that encode functions by either (i) randomly generating the programs or (ii) using programs evolved by a genetic programming instance that uses randomized targets;
  obtaining a list of randomly generated test inputs; generating a target dataset that includes initial input-output pairs of randomly generated binary strings;
  applying a fitness function to assign a fitness score to each program in the parent population, wherein the fitness score represents at least an ability of a respective program in the parent population to match the initial input-output pairs of the target dataset;
  initializing a seed list with copies of the program in the parent population that satisfy a novelty condition, wherein the novelty condition is representative of an ability of a program to produce distinct and unique output for the list of randomly generated test inputs;
  determining if a terminating condition of the seed list has been satisfied, wherein the terminating condition is representative of an ability of one or more programs in the seed list to solve one or more genetic programming instances;
  in accordance with a determination that the terminating condition has not been satisfied:
  applying at least one genetic operator to the parent population to obtain a current offspring population of programs, wherein the at least one genetic operator includes operators applied to the parent population to grow the seed list, based on fitness scores of the programs in the parent population, to solve the one or more genetic programming instances; and
  repeating steps of:
    generating a new target dataset that includes new input-output pairs of randomly generated binary strings;
    applying the fitness function to assign a new fitness score to each program in the current offspring population, wherein the new fitness score represents at least an ability of a respective program in the current offspring population to match the new input-output pairs of the new target dataset;
    appending, to the seed list, copies of the programs in the current offspring population that satisfy the novelty condition; and
    applying the at least one genetic operator to the current offspring population to obtain a new offspring population of programs and setting the new offspring population of programs as the current offspring population;
  until said termination condition is satisfied.

* * * * *